US00PP17273P2

(12) United States Plant Patent
Drewlow

(10) Patent No.: US PP17,273 P2
(45) Date of Patent: Dec. 12, 2006

(54) ***KALANCHOE* PLANT NAMED 'FOREVER MIDI TWILIGHT'**

(50) Latin Name: *Kalanchoe blossfeldiana*
Varietal Denomination: Forever Midi Twilight

(75) Inventor: Lyndon W. Drewlow, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 11/177,534

(22) Filed: Jul. 8, 2005

(51) Int. Cl.
*A01H 5/00* (2006.01)

(52) U.S. Cl. ..... Plt./335
(58) Field of Classification Search ..... Plt./338, Plt./335
See application file for complete search history.

(56) References Cited

U.S. PATENT DOCUMENTS

PP12,299 P2 * 12/2001 Jepsen ..... Plt./338

OTHER PUBLICATIONS

"Twilight", available at: http://oglevee.com/articles/Varieties/Kalanchoes/forever/midi/twilight_info.htm.*

* cited by examiner

*Primary Examiner*—Wendy Haas
(74) *Attorney, Agent, or Firm*—The Webb Law Firm

(57) ABSTRACT

'Forever Midi Twilight' is a new variety of *kalanchoe* that exhibits larger flowers that open as bright yellow and then fade to light yellow and then to pink.

1 Drawing Sheet

Botanical classification: *Kalanchoe blossfeldiana.*
Varietal denomination: 'Forever Midi Twilight'.

BACKGROUND OF THE INVENTION

The present invention comprises a new and distinct cultivar of *Kalanchoe blossfeldiana* known by the varietal name 'Forever Midi Twilight'. The new variety was discovered in Lompoc, Calif. The new variety is a result of cross breeding Seedling #98-144-4 (female parent) (unpatented) and Seedling #97-200-3 (male parent) (unpatented). The purpose of the breeding program was to develop a highly self-branching cultivar with large flowers and an early response time. Further, a new variety with flowers that open as yellow and fade to light yellow and then to pink was desired. Comparisons between the new variety and its parents cannot be made, as the parental varieties no longer exist. The new variety was first asexually reproduced by tip cuttings in Lompoc, Calif. The new variety has been trial and field tested and has been found to retain its distinctive characteristics and remain true to type through successive propagations. Characteristics that distinguish the new variety from others known to the breeder include:

- Large-flowers with a semi-compact growth habit;
- Distinct flower color as it opens as bright yellow and fades to light yellow to light pink;
- Early to flower with a 9–9½ week response time under winter conditions and 8½–9 weeks under summer conditions after the start of short days;
- Large inflorescences can be finished in 10 cm. containers without growth regulators;
- Does not heat delay when night temperatures are above 22° C. during short day treatments to induce flowering;

- Long keeping quality of cultivar in part due to the fact that the inflorescence is a cyme with an indeterminate growth habit;
- Highly self-branching and basal breaks without a pinch; and
- Tolerant to common insect and disease problems.

The new variety was grown in a 10 cm. container in Lompoc, Calif. under Dynaglass with 30% shade. The new variety initiates roots in 10 days in the summer and 12 days in the winter at 21° C. The new variety exhibits developed roots at 21 days at an average temperature of 21° C. Its rooting habit is dense and freely branching with fine and fibrous roots.

DESCRIPTION OF THE PLANT

Figure 1:
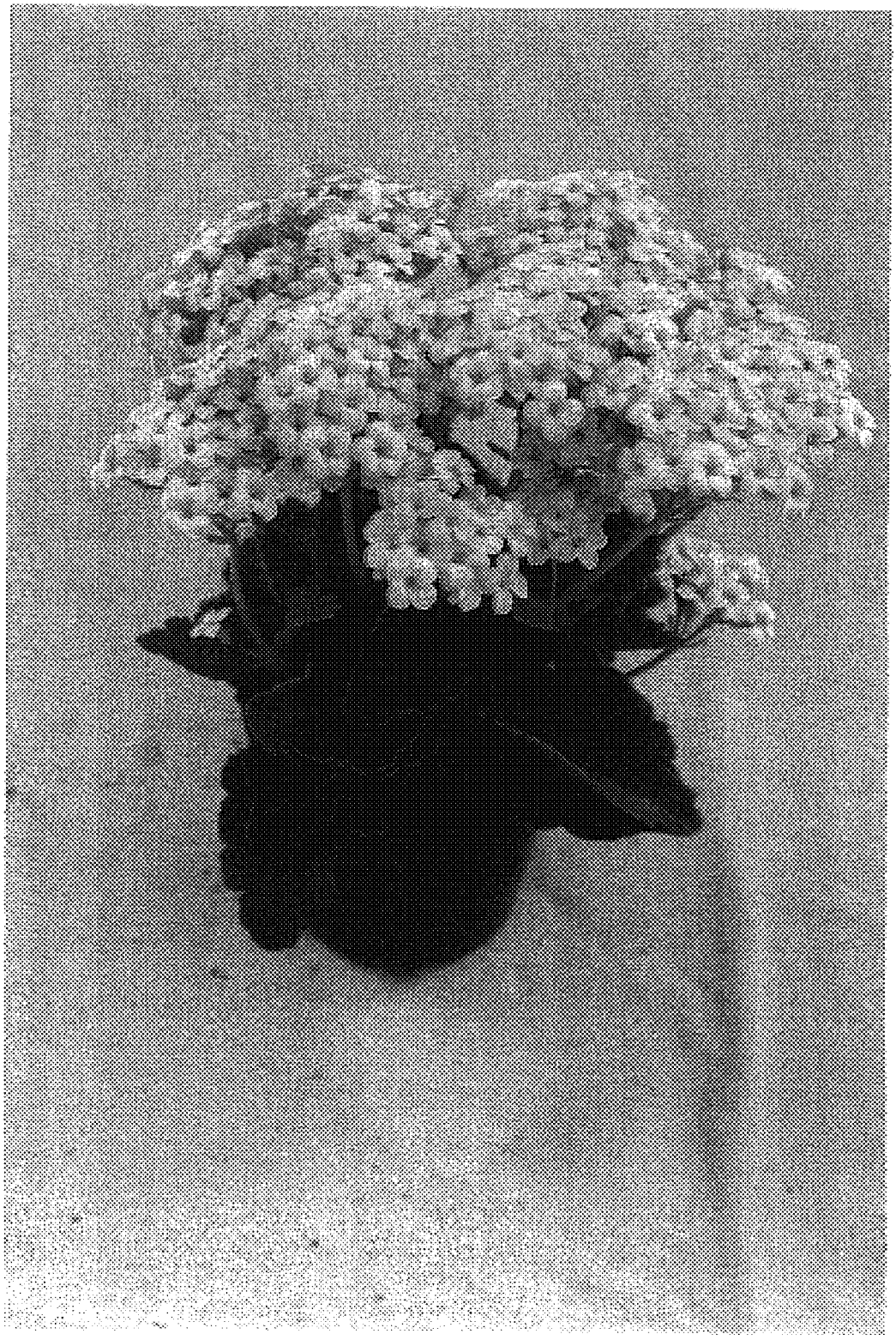
FIG. 1 illustrates the new variety, with the color being as nearly true as is possible with color illustrations of this type.

The following detailed description sets forth the characteristics of the new cultivar. The data which defines these characteristics were collected by asexual reproductions carried out in Lompoc, Calif. The color readings were taken indoors under 3500–4000 foot candles of light. The new variety was twelve weeks from the start of short days when described. Color references are primarily to the 1966 R.H.S. Colour Chart of The Royal Horticultural Society of London.

PLANT

Form: Mounded to semi-upright.
Height (from soil to top of flowers): 18 cm.
Plant diameter: 22–24 cm.
Vigor: Vigorous.

Branching habit: Highly self-branching.
Main stem:
*Color.*—145 A.
*Texture.*—Glabrous.
*Length.*—8–10 cm.
*Diameter.*—10–12 mm near soil line.
*Internode length.*—1–2 cm, but varies with location on stem.
*Strength.*—Strong.
Lateral branches:
*Color.*—145 A.
*Texture.*—Glabrous.
*Length.*—Basal: 18–20 cm. Upper: 13–15 cm.
*Diameter.*—4 mm.
*Internode length.*—5–7 cm, but the environment can greatly effect the length.
*Strength.*—Strong.
*Quantity.*—8–10.
Foliage:
*Arrangement.*—Opposite.
*Number of leaves per stem.*—Main: 10–12. Laterals: 2–4.
*Size of leaf.*—Length: 8–10 cm. Width: 8–10 cm.
*Shape of leaf.*—Ovate.
*Shape of apex.*—Acute.
*Shape of base.*—Acute to truncate.
*Texture.*—Glabrous, coriaceous and succulent.
*Aspect.*—90° to main stem; slightly hanging down.
*Margin type.*—Crenate, moderately lobed.
*Fragrance.*—None.
*Color.*—Young leaves: Upper surface: 146C. Lower surface: 146C. Mature leaves: Upper surface: 147B. Lower surface: 147B.
*Petiole.*—Length: 8–10 mm. Diameter: 8 mm. Color: 146A. Texture: Glabrous.
*Veins.*—Venation pattern: Pinnate. Color: Upper surface: 147A. Lower surface: 147B.

FLOWER

Natural flowering season at specified locations: Early January in Lompoc, Calif.
Flower type and habit: Epigenous-terminal flower on main stem opens first, followed by terminal buds on laterals.
Number of flowers per plant: 250 or more.
Time of day of flower opening: Morning.
Fragrance: None.
Longevity: Up to 2 weeks — Environment effects keeping quality.
Flower height: 14 mm.
Flower diameter: 18 mm.
Bud:
*Stage of development when described.*—18 mm.
*Shape.*—Oblong.
*Diameter.*—3 mm.
*Length.*—16 mm.
*Color.*—146D at the calyx area and 36A near tip.
Corolla:
*Diameter.*—18 mm.
*Depth.*—14 mm.
*Tube.*—
*Length.*—7 mm.
*Diameter.*—3 mm.
Petals:
*Arrangement.*—Whorl of 4 fused.
*Quantity.*—4.
*Length.*—10 mm non fused part.
*Width.*—7 mm.
*Shape.*—Ovate to round.
*Apex.*—Cuspidate.
*Base.*—Rounded.
*Margin.*—Entire.
*Texture.*—Smooth, soft.
*Color.*—Upper surface: 11B with areas of 11A. Lower surface: 11D with areas of 11C.
Sepals:
*Quantity.*—4.
*Shape.*—Lanceolate.
*Length.*—8 mm.
*Width.*—2 mm.
*Color.*—145A.
Peduncles:
*Length.*—20 mm.
*Diameter.*—2 mm.
*Color.*—146D.
*Texture.*—Glabrous.
*Orientation.*—45° Angle.
*Strength.*—Strong.
Pedicels:
*Length.*—3 mm.
*Width.*—1 mm.
*Color.*—146D.
Disease resistance: Resistant.
Weather tolerance: Tolerant.
Lasting quality:
*On plant.*—4–6 weeks if properly cared for.
*Of cut flowers.*—Not usually used as cut flowers.
Seed production and description: Not applicable.
Fruit production and description: Not applicable.

REPRODUCTIVE ORGANS

Stamens:
*Number (per flower).*—8.
*Filament length.*—Less than 1 mm.
*Anthers.*—Shape: Flat Elliptical. Length: Less than 1 mm. Color: Yellow-green.
*Pollen.*—Color: Yellow. Amount: Abundant.
Pistils:
*Length.*—10 mm.
*Styles.*—Length: 4 mm. Color: Light yellow-green.
*Stigma.*—Shape: Flat. Color: White when mature. Ovary color: 146C.

I claim:

1. A new and distinct variety of *kalanchoe* plant named 'Forever Midi Twilight' as described and illustrated.

* * * * *